United States Patent
Aoi

(10) Patent No.: US 10,798,333 B2
(45) Date of Patent: Oct. 6, 2020

(54) CELL OBSERVATION SYSTEM

(71) Applicant: Shimadzu Corporation, Kyoto (JP)

(72) Inventor: Yusuke Aoi, Kyotanabe (JP)

(73) Assignee: Shimadzu Corporation, Kyoto (JP)

( * ) Notice: Subject to any disclaimer, the term of this patent is extended or adjusted under 35 U.S.C. 154(b) by 121 days.

(21) Appl. No.: 15/906,390

(22) Filed: Feb. 27, 2018

(65) Prior Publication Data

US 2018/0249117 A1 Aug. 30, 2018

(30) Foreign Application Priority Data

Feb. 28, 2017 (JP) .................................. 2017-035798

(51) Int. Cl.
*H04N 7/01* (2006.01)
*H04N 5/445* (2011.01)
(Continued)

(52) U.S. Cl.
CPC ....... *H04N 7/0117* (2013.01); *G01N 33/4833* (2013.01); *G02B 21/0004* (2013.01); *G02B 21/368* (2013.01); *G03H 1/0005* (2013.01); *G03H 1/0443* (2013.01); *G06T 1/0007* (2013.01); *G06T 3/0012* (2013.01); *H04L 67/02* (2013.01); *H04L 67/12* (2013.01); *H04N 5/4403* (2013.01); *H04N 5/44591* (2013.01);
(Continued)

(58) Field of Classification Search
CPC . H04N 7/0117; G02B 21/367; G01N 33/4833
See application file for complete search history.

(56) References Cited

U.S. PATENT DOCUMENTS 7,812,959 B1 * 10/2010 Kim ...................... G01B 9/021
356/458
2002/0089502 A1 * 7/2002 Matchen ................... G06T 3/40
345/428
(Continued)

FOREIGN PATENT DOCUMENTS

CN 1500250 A 5/2004
CN 105956395 A 9/2016
(Continued)

OTHER PUBLICATIONS

Office Action dated Apr. 22, 2019 in corresponding Chinese Application No. 2018101688591; 20 pages including English-language translation.
(Continued)

*Primary Examiner* — Zhubing Ren
(74) *Attorney, Agent, or Firm* — Maier & Maier, PLLC

(57) ABSTRACT

An image creation unit of a server creates and stores a plurality of phase images or the like having different resolutions on the basis of holographic data collected by a measuring terminal. In response to an image transmission request according to an operation, an image transmission processing unit of the server extracts data of an image corresponding to an observation range after the movement from an image of an appropriate resolution and transmits the data to the browsing terminal. In the browsing terminal, a display image is formed by overlaying a high-resolution phase image corresponding to only an observation range to be displayed on low-resolution phase image of an observation target area.

8 Claims, 5 Drawing Sheets

(51) Int. Cl.

| | | |
|---|---|---|
| *H04N 5/44* | (2011.01) | |
| *G06T 1/00* | (2006.01) | |
| *G02B 21/36* | (2006.01) | |
| *G03H 1/00* | (2006.01) | |
| *G01N 33/483* | (2006.01) | |
| *H04L 29/08* | (2006.01) | |
| *G02B 21/00* | (2006.01) | |
| *G03H 1/04* | (2006.01) | |
| *G06T 3/00* | (2006.01) | |
| *G06F 3/0484* | (2013.01) | |
| *H04N 1/64* | (2006.01) | |

(52) U.S. Cl.
 CPC ............... *G03H 2001/005* (2013.01); *G03H 2001/0447* (2013.01); *G06F 3/04845* (2013.01); *H04N 1/64* (2013.01)

(56) References Cited

U.S. PATENT DOCUMENTS

| | | | |
|---|---|---|---|
| 2004/0145679 A1 | 7/2004 | Kim | |
| 2005/0281484 A1* | 12/2005 | Perz | G02B 21/365 |
| | | | 382/294 |
| 2010/0060897 A1 | 3/2010 | Gustafsson | |
| 2011/0128299 A1 | 6/2011 | Wakita et al. | |
| 2012/0162228 A1* | 6/2012 | Yamane | G06F 19/321 |
| | | | 345/428 |
| 2015/0130809 A1 | 5/2015 | Tagami et al. | |

FOREIGN PATENT DOCUMENTS

| | | |
|---|---|---|
| JP | 2005-117640 A | 4/2005 |
| JP | 2009-521216 A | 6/2006 |
| JP | 2011-118005 A | 6/2011 |
| JP | 2014-013263 A | 1/2014 |
| JP | 2015-152650 A | 8/2015 |
| WO | 2016/084420 A1 | 7/2017 |

OTHER PUBLICATIONS

Office Action dated Mar. 31, 2020 in corresponding Japanese Application No. 2017-035798; 7 pages.

* cited by examiner (a) LOW RESOLUTION (b) MIDDLE RESOLUTION (c) HIGH RESOLUTION (a) RECEIVED (BEFORE-MOVEMENT) IMAGE DATA (b)

(c)

(e) AFTER-MOVEMENT IMAGE DATA

FIG.7 (a) ONE IMAGE DISPLAY
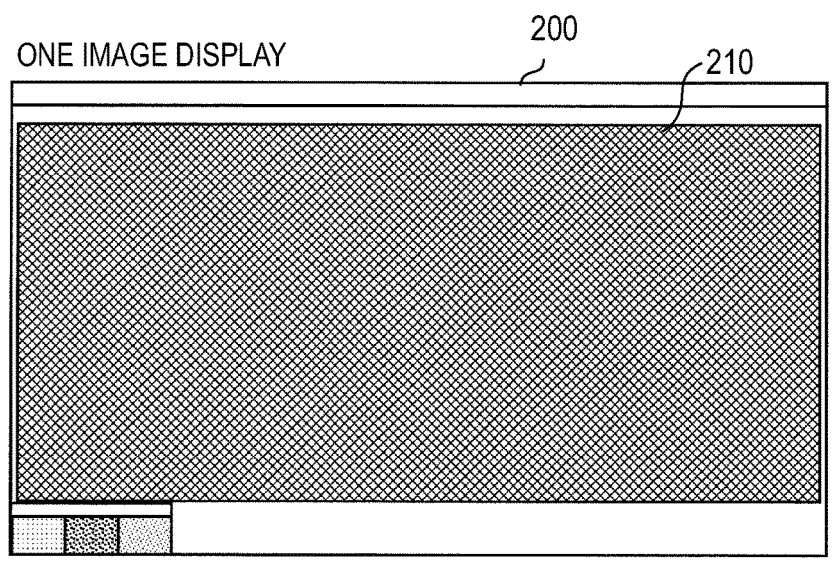
FIG.7 (b) TWO-IMAGE SPLIT DISPLAY
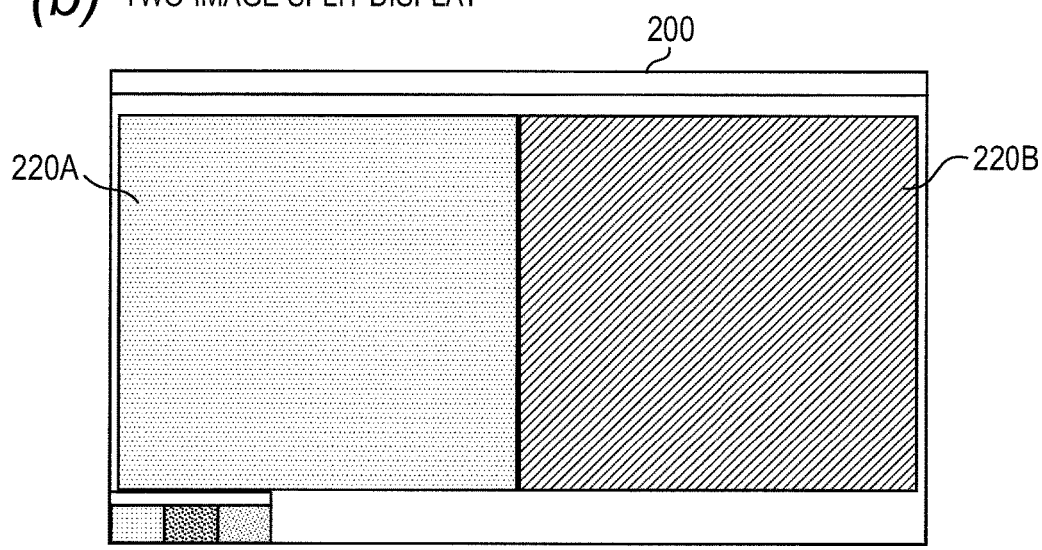
FIG.7 (c) FOUR-IMAGE SPLIT DISPLAY
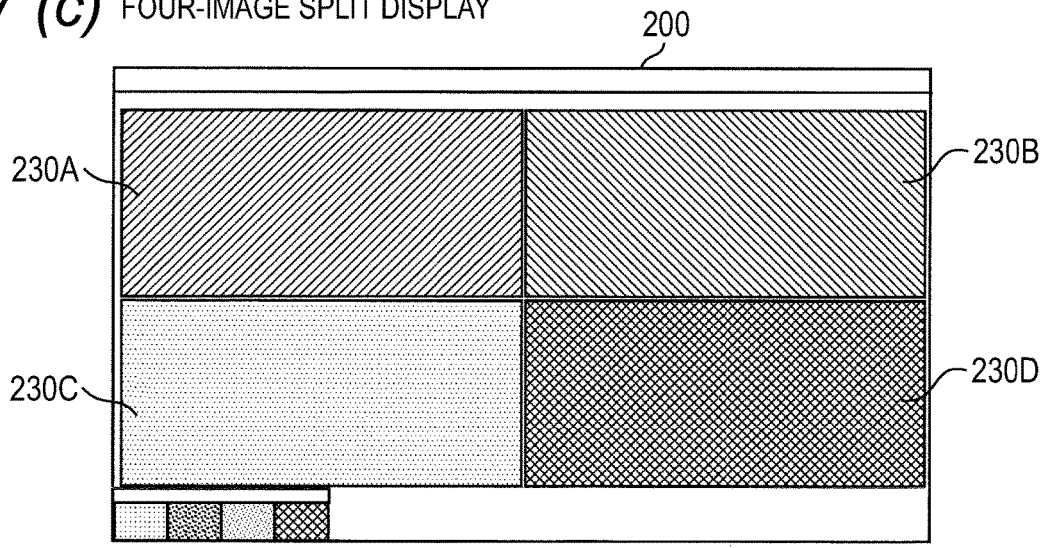

CELL OBSERVATION SYSTEM

FIELD

The present invention relates to a cell observation system for observing cells, and more particularly, to a cell observation system suitable for observing biological cells using a phase contrast microscopic image obtained by a phase contrast microscope, a phase image created on the basis of a hologram by a digital holographic microscope, and the like.

BACKGROUND ART

In the field of regenerative medicine, studies using pluripotent stem cells such as iPS cells and ES cells have been actively conducted in recent years. In general, biological cells are colorless and transparent and difficult to observe with a normal optical microscope. Therefore, a phase contrast microscope is widely used to observe biological cells (see, Patent Literature 1 and the like). For the phase contrast microscope, when illumination light passes through an observation target, a two-dimensional observation image can be created with contrast of light and dark, on the basis of a difference between an optical path of light diffracted by the object and an optical path of direct light of the illumination. The observation image may be conventionally called a phase contrast image. However, strictly speaking, the observation image includes not only phase difference information of light but also a part of information of a light intensity (an amplitude of light), so the observation image will be referred to as a phase contrast microscopic image in the present disclosure.

Meanwhile, recently, an apparatus has been developed that acquires phase information and amplitude information of light by using holography technology, and creates a phase image and an intensity image of the observation target on the basis of the information. The apparatus is referred to as a holographic microscope or a digital holographic microscope (see Patent Literature 2 and the like).

In the holographic microscope, an interference fringe (hologram) is obtained which is formed on a detection surface of an image sensor or the like by object light that comes from a light source and is reflected from or transmitted through a surface of the observation target and reference light that directly reaches from the light source. By executing predetermined arithmetic processing based on the hologram, a phase image, an intensity image, a pseudo phase image corresponding to a phase contrast microscopic image in a phase contrast microscope, or the like is created as a reproduction image of the observation target.

When observing cells in culture using any of the microscopes as described above, it is necessary to observe a single cell culture plate or a plurality of cell culture plates as a whole and also necessary to enlarge cells in a single cell culture plate, in other words, observe the cells finely at high magnification. Therefore, in a cell observation system in which such a microscope is used, it is common to perform photographing on a wide area with a resolution as high as possible when acquiring a phase contrast microscopic image or a hologram of a cell to be observed, and to perform image processing by lowering the resolution appropriately according to a resolution requested by a user when creating a display image (see Patent Literature 3).

As described above, for example, when data is acquired with such a high resolution that individual cells can be minutely observed with respect to an entire observation target area where a plurality of cell culture plates come into sight, a total amount of the data is enormous. For this reason, a storage device with a large storage capacity is required to store the data acquired for a large number of samples. Further, an enormous amount of calculation is required for calculation of phase information and intensity information based on hologram data obtained by a holographic microscope and imaging of calculation results thereof. Therefore, it takes a great deal of time for the calculation, making it difficult to perform an analysis work efficiently, with capability of a CPU used in a general personal computer (PC). Therefore, in the field of such cell observation, it has been conventionally proposed to use a computer system in which a PC connected to a microscopic observation unit is a terminal device and the terminal device and a server which is a high-performance computer are connected via a communication network such as the Internet or an intranet (see Patent Literatures 3, 4 and the like). In such a system, the terminal device merely performs a work with a relatively small load, such as acquisition of data, and the high-performance server performs a work with a large load such as arithmetic processing or image creation processing for a large amount of data or management of a large amount of data.

However, such a cell observation system also has the following problems.

When a user observes a cell with a browsing terminal (entity is a PC) connected to a server via a communication network, it is frequently performed to search for a portion of interest while enlarging a very small portion of the entire wide observation target area with high magnification or repeat observations of high magnification and low magnification. Since a data amount of the high-resolution image for the entire observation target area is enormous, it takes time to transmit and receive such a large amount of image data when it is attempted to transfer the data from the server to the browsing terminal, lowering a responsiveness of the image display on the browsing terminal. In other words, even when the user moves or enlarges or reduces a display range of an image being observed on a display screen, it takes time for the display image to be updated, causing a problem of deteriorating a workability.

Further, in the cell observation system using the holographic microscope as described above, there is a strong demand for obtaining not only the phase image but also other kinds of images such as an intensity image and a pseudo phase image and observing those plural types of images simultaneously. However, as the number of types of images displayed on the browsing terminal increases, the amount of data to be transmitted and received between the server and the browsing terminal increases accordingly, so it takes more time for data transfer, further lowering the responsiveness of image display.

[Patent Literature 1] JP-A-2015-152650
[Patent Literature 2] International Patent Publication No. 2016/084420
[Patent Literature 3] JP-A-2005-117640
[Patent Literature 4] JP-A-2014-13263

SUMMARY

The present invention has been made in view of the above problems, and mainly intends to improve responsiveness to operations such as movement, enlargement or reduction of a range of a display image, that is, to improve an update speed of the display image, thereby enabling an efficient observation, when looking at images such as high-resolution phase images on the a browsing terminal for image browsing in a cell observation system in which a server for data processing and the browsing terminal are connected via a communication network.

Further, the present invention intends to provide a cell observation system capable of enhancing responsiveness of image display even when a plurality of types of images are simultaneously displayed and observed on a browsing terminal.

In order to solve the above problems, the present invention provides a cell observation system in which a server capable of creating an image relating to an observation target on the basis of data obtained by a microscopic observation unit with respect to the observation target and a browsing terminal for browsing the image created by the server on a screen of a display unit are connected via a communication network, in which the server includes:

a1) an image creation unit that creates images having different resolutions at a plurality of levels with respect to an entire observation target area to be observed by the microscopic observation unit on the basis of the data obtained by the microscopic observation unit, and stores the images in an image storage unit; and a2) an image transmission processing unit that extracts image information of all or a part of the images having a predetermined resolution stored in the image storage unit and transmits the extracted image information to the browsing terminal, in response to an image transmission request from the browsing terminal, and in which the browsing terminal includes:

b1) an operation unit that allows a user to move or enlarge/reduce a display range of the observation target displayed on the screen of the display unit by the user;

b2) an image transmission request unit that transmits an image transmission request to the server so as to transmit an image according to a resolution and a display range after the movement or the enlargement/reduction by an operation using the operation unit;

b3) a display image formation unit that includes a storage unit which stores a low-resolution image having a relatively low resolution and corresponding to the entire observation target area or a range wider than the display range of the observation target displayed on the screen of the display unit at least at that point in the observation target area, has a function of forming a display image by overlaying a high-resolution image having a relatively high resolution and corresponding to the display range of the observation target displayed on the screen of the display unit at that time on the low-resolution image, forms the display image on the basis of at least the low-resolution image until the image information arrives from the server in response to the image transmission request after the movement or after the enlargement/reduction by the operation using the operation unit, and forms the display image by overlaying on the low-resolution image a new high-resolution image based on the image information when the image information is obtained from the server in response to the image transmission request.

The browsing terminal is a computer such as a personal computer (PC), a tablet type terminal (tablet type PC) or a smartphone, or a device equivalent thereto, and a function of each part thereof may be realized by a program installed in such a device. Further, not only one browsing terminal but also a plurality of browsing terminals may be connected via a communication network to one server.

Further, the microscopic observation unit is typically a holographic microscope or a phase contrast microscope.

In a case where the microscopic observation unit is a holographic microscope, the data obtained by the microscopic observation unit is hologram data, and the image creation unit creates a phase image, an intensity image, a pseudo phase image, an optical path length difference image or the like with respect to the entire observation target area on the basis of the hologram data.

Further, in a case where the microscopic observation unit is a phase contrast microscope, the data obtained by the microscopic observation unit is phase difference value data, and the image creation unit may create a phase difference microscopic image with respect to the entire observation target area on the basis of the data.

In the cell observation system according to the present invention, for example, a control PC directly connected to the microscopic observation unit and a server are connected via a communication network, and the data obtained at the microscopic observation unit is transmitted from the control PC to the server through the communication network. This control PC may also serve as a browsing terminal. However, a means by which the server collects the data obtained by the microscopic observation unit is not limited thereto, but, for example, the data in the microscopic observation unit may be temporarily recorded in a portable recording medium and the server may read the data from the medium.

For example, when the microscopic observation unit is a holographic microscope, in the server of the cell observation system according to the present invention, the image creation unit calculates phase information, intensity information, and the like in the observation target area based on the acquired hologram data, and, on the basis of such information, creates a plurality of phase images and intensity images having different resolutions with respect to the entire observation target area. Then, image data constituting thus created plurality of images with different resolutions generated is stored in the image storage unit. The resolution of the image created by the image creation unit may be appropriately determined in advance according to a screen resolution (the number of pixels) and the like of the display unit of the browsing terminal which is assumed to be used, but a maximum resolution of the created image is determined in principle by a spatial resolution of the acquired hologram data.

On the other hand, the display image formation unit in the browsing terminal, for example, forms the display image to be displayed on the screen of the display unit by overlaying an image having relatively high resolution and corresponding to the display range (the entire observation target area or a range narrower than the entire observation target area) of the observation target displayed on the screen of the display unit at that time on the image having relatively low resolution and corresponding to the entire observation target area. Thus, for example, when displaying an enlarged image of a portion of the cells in the cell culture plate, the display image is formed by overlaying high-resolution image in a narrow range of the cells to which an observer is paying attention on the low-resolution image corresponding to the entire observation target area such as an entire cell culture plate. Thus, the high-resolution image in the narrow range of the cells the observer is paying attention to is displayed on the screen of the display unit.

In this state, when the observer performs a predetermined operation on the operating unit of the browsing terminal, for example, in order to move the range to be observed (the range of the display image displayed on the screen of the display unit), the image transmission request unit transmits the image transmission request to the server so that the server transmits the image according to the display range and the resolution according to the operation. Specifically, for example, the image transmission request is transmitted together with position information or information on a movement amount and a movement direction with respect to a movement destination in the entire observation target area and information on the number of pixels of the image that can be displayed according to a screen resolution of the display unit as necessary. The image transmission processing unit in the server, in response to the transmitted image transmission request, selects an image of the entire observation target area having a resolution matching designated pixel number information from the images stored in the image storage unit and extracts a partial image corresponding to a designated range in the selected image, and transmits image data forming the image to the browsing terminal which is a sender of the image transmission request.

While the observer is moving the observation range with the operation unit, that is, before the destination is determined, the storage unit of the display image formation unit stores low-resolution images corresponding to the observation range at respective points in time during the movement are stored, but high-resolution images corresponding to the ranges are not necessarily stored. Therefore, until the image information corresponding to the image transmission request arrives from the server, the display image formation unit forms and displays the display image corresponding to the observation range at each point in time during the movement on the basis of the low-resolution image stored in the storage unit. When the image information arrives from the server in response to the image transmission request, the display image is formed by overlaying the high-resolution image on the low-resolution image on the basis of the received image information. Therefore, the low-resolution image corresponding to the observation range at each point in time during the movement is continuously displayed while the observer is moving the observation range with the operation unit, and as soon as a movement destination is fixed, high-resolution image corresponding to an observation range of the movement destination is displayed.

A data amount of an image data constituting a high-resolution image of high magnification is large. However, when a resolution of a display image needs to be increased, an observation range thereof is narrow, such that an amount of the image data transmitted from the server to the browsing terminal is small. Therefore, time required for transmission and reception of the image data is short, and when the movement destination of the observation range is determined, it is possible to quickly display the high-resolution image corresponding to that range. Further, while the observer is moving the observation range, an image corresponding to the observation range that is being moved is always displayed although it has low resolution. Thus, the observer can decide the range to be observed while confirming the image.

In the case of enlargement/reduction rather than movement of the observation range, a resolution of the image after the enlargement/reduction may change depending on a degree of the enlargement/reduction. However, basically, the display during or after the enlargement/reduction operation is performed with the same operation as that at the time of the movement.

Further, when the microscopic observation unit is a holographic microscope in the cell observation system according to the present invention, the server creates two or more types of cell observation images of the phase image, the intensity image, or the pseudo phase image, and the display image formation unit may be configured to simultaneously display a plurality of types of cell observation images for the same area in the observation target area on the screen of the display unit, and to move or enlarge/reduce the cell observation image and the displayed other cell observation images in conjunction with each other in response to an operation of the movement or the enlargement/reduction on any displayed cell observation image.

For example, information that can be obtained from the phase image differs from information that can be obtained from the intensity image. However, according to the above-described configuration, it is possible to always confirm the phase image and the intensity image of an observation range simultaneously.

In the cell observation system having the above-described configuration, the image transmission processing unit may transmit a size of a display area of each of the plurality of types of cell observation images displayed on the screen of the display unit of the browsing terminal and image information of a resolution corresponding to a screen resolution of the display unit to the browsing terminal.

As a matter of course, as the number of images displayed on one screen increases, the number of pixels allocated per display image decreases. Therefore, even if the observation ranges have the same size, if the number of images to be displayed on one screen is large, the resolution of the image can be lowered. In view of this, the image transmission processing unit transmits the size of the display area of each of the plurality of kinds of cell observation images displayed on the screen of the display unit of the browsing terminal and the image information of the resolution corresponding to the screen resolution of the display unit to the browsing terminal. Thus, for example, even when the phase image and the intensity image are displayed at the same time, the amount of image data to be transmitted from the server to the browsing terminal may be suppressed to the same extent as when only the phase image is displayed, securing a high display responsiveness.

Further, in addition to displaying the phase image, the intensity image, and the like created on the basis of the same hologram data simultaneously on the screen of the display unit, the cell observation system according to the present invention may display a plurality of images related to each other simultaneously on the screen of the display unit. More specifically, the display image formation unit may be configured to form images on the basis of image information acquired at different dates and times for the same area of the same observation target and display the plurality of images simultaneously on the screen of the display unit.

Also in this case, when the movement or the enlargement/reduction operation is performed with respect to any one of a plurality of displayed images, not only the pertinent image but also other images in conjunction with the pertinent image may be moved or enlarged/reduced.

When observing the cells in culture, it is necessary to continuously observe the same cell culture plate daily for a certain period of time and compare states of the cells, but, according to the above configuration, it is possible to easily and accurately compare images obtained at different dates and times.

According to the cell observation system of the present invention, when the observer moves or enlarges/reduces the observation range of the phase image or the like displayed with high resolution in the browsing terminal, high-resolution phase image and the like can be quickly displayed on the screen after the operation. Thus, for example, it is possible to quickly find an area to which the observer is paying attention in a wide observation target area and to perform cell observation efficiently.

BRIEF DESCRIPTION OF THE DRAWINGS

FIG. 7(a) is a diagram illustrating one-image display; FIG. 7(b) is a diagram illustrating two-image split display; and FIG. 7(c) is a diagram illustrating four-image split display in the cell observation system of the present embodiment.

DETAILED DESCRIPTION

Hereinafter, an embodiment of a cell observation system according to the present invention will be described with reference to the accompanying drawings.

Figure 1:
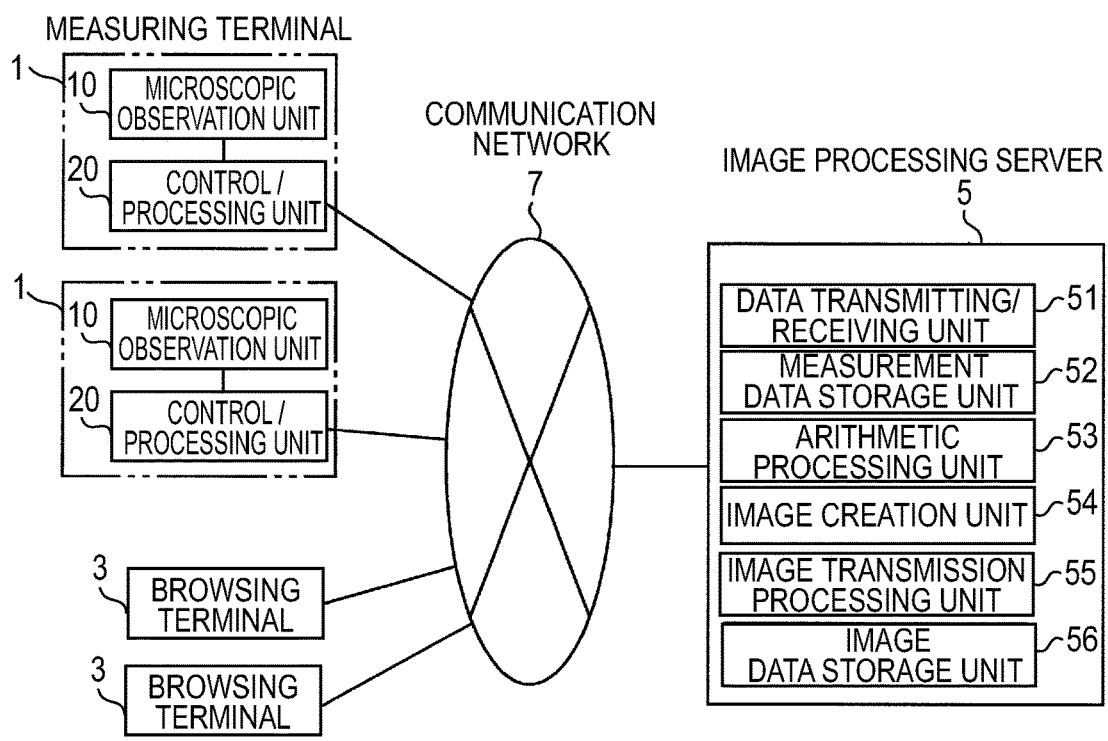
FIG. 1 is an overall configuration diagram of an embodiment of a cell observation system according to the present invention.
Figure 2:
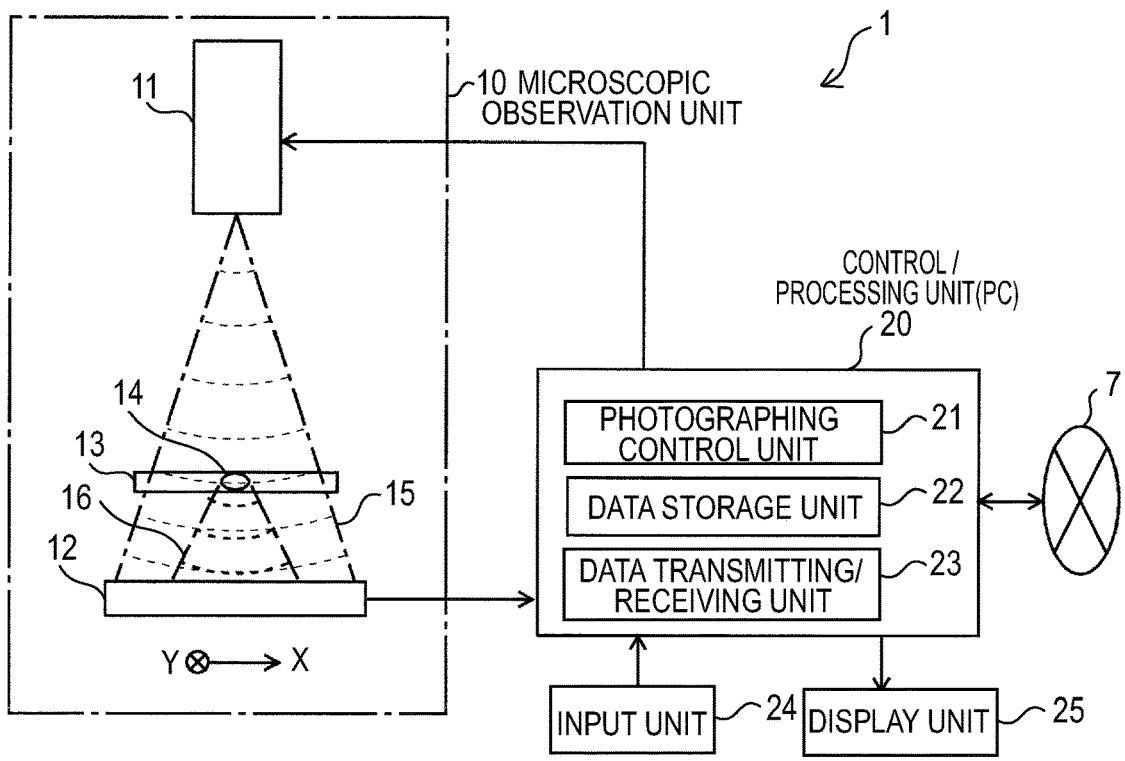
FIG. 2 is a schematic configuration diagram of a measuring terminal in the cell observation system of the present embodiment.
Figure 3:
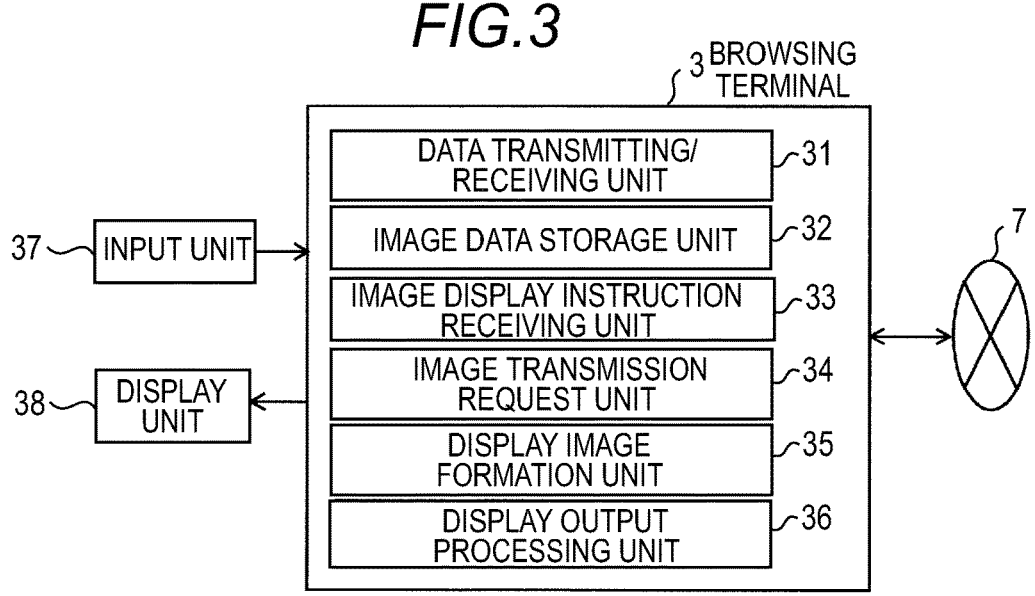
FIG. 3 is a schematic configuration diagram of a browsing terminal in the cell observation system of the present embodiment.

FIG. 1 is an overall configuration diagram of a cell observation system of the present embodiment, FIG. 2 is a schematic configuration diagram of a measuring terminal in the cell observation system of the present embodiment, and FIG. 3 is a schematic configuration diagram of the browsing terminal in the cell observation system of the present embodiment.

The cell observation system of the present embodiment includes a measuring terminal 1, a browsing terminal 3, and an image processing server 5, which are connected via a communication network 7 such as an internet or an intranet. In FIG. 1, two measuring terminals 1 and two browsing terminals 3 are illustrated, but each of them can be provided in an appropriate number.

The image processing server 5 is a computer having a higher performance than a personal computer (PC) generally called a workstation. As illustrated in FIG. 1, as functional blocks realized by dedicated software installed in the computer, there are provided a data transmitting/receiving unit 51, a measurement data storage unit 52, an arithmetic processing unit 53, an image creation unit 54, an image transmission processing unit 55, an image data storage unit 56, and the like.

The measuring terminal 1 includes a microscopic observation unit 10 and a control/processing unit 20. In this example, the microscopic observation unit 10 is an in-line holographic microscope (IHM) and includes a light source unit 11 including a laser diode or the like and an image sensor 12, as illustrated in FIG. 2. Between the light source unit 11 and the image sensor 12, a cell culture plate 13 including cells 14 as observation targets is disposed. An entity of the control/processing unit 20 is a personal computer (PC) that controls an operation of the microscopic observation unit 10 and processes data acquired by the microscopic observation unit 10, and there are provided a photographing control unit 21, a data storage unit 22, and a data transmitting/receiving unit as functional blocks realized by dedicated software installed in the PC. In addition, an input unit 24 and a display unit 25 as a user interface are connected to the control/processing unit 20.

Like the control/processing unit 20 in the measuring terminal 1, an entity of the browsing terminal 3 is a general PC. Further, as functional blocks realized by dedicated software installed in the PC, there are provided a data transmitting/receiving unit 31, an image data storage unit 32, an image display instruction receiving unit 33, an image transmission request unit 34, a display image formation unit 35, and a display output processing unit 36. Further, an input unit 37 as a user interface and display unit 38 are connected to the browsing terminal 3.

The browsing terminal 3 may be a variety of information terminal devices such as a tablet PC and a smartphone, which are substantial computers equipped with CPU, ROM, RAM and the like.

Further, a PC functioning as the control/processing unit 20 of the measuring terminal 1 may have a function of the browsing terminal 3. In this case, the control/processing unit 20 of the measuring terminal 1 may also perform an image browsing to be described later in a similar way to that of the browsing terminal 3.

First, an operation at the time of collecting data on a cell to be observed in the cell observation system of the present example will be described.

In FIG. 2, an operator sets a cell culture plate 13 including a biological cell (a pluripotent cell) 14 to be observed at a predetermined position, inputs information such as an identification number for identifying the cell culture plate 13 and measurement date and time from an input unit 24, and instructs an execution of measurement. Upon receiving the instruction, the photographing control unit 21 controls the microscopic observation unit 10 to acquire data, as described below.

That is, under the control of the photographing control unit 21, the light source unit 11 irradiates a predetermined area of the cell culture plate 13 with coherent light having a spread of a small angle of about 10 degrees. The light (object light 16) transmitted through the cell culture plate 13 and the cell 14 reaches the image sensor 12 while interfering with light (reference light 15) transmitted through an area close to the cell 14 on the cell culture plate 13. The object light 16 is a light whose phase has changed when it passes through the cell 14. However, the reference light 15 does not pass through the cell 14, so it does not undergo a phase change due to the cell 14. Therefore, an interference image (hologram) of the object light 16 whose phase has been changed by the cell 14 and the reference light 15 whose phase is not changed is formed on a detection surface (an image plane) of the image sensor 12.

The cell culture plate 13 is sequentially moved in two axial directions of an X axis and a Y axis (in a plane perpendicular to the paper surface of FIG. 2) by a moving mechanism (not illustrated). Thus, a hologram for each small area in a wide observation area is repeatedly acquired and hologram data for the entire observation area can be collected by moving an irradiation area (an observation area) of the coherent light emitted from the light source unit 11 stepwise on the cell culture plate 13.

As described above, the hologram data (a two-dimensional light intensity distribution data of the hologram formed on the detection surface of the image sensor 12) obtained by the microscopic observation unit 10 is temporarily stored in the data storage unit 22 in the control/processing unit 20. The data transmitting/receiving unit 23 sequentially transfers the hologram data stored in the data storage unit 22, together with attribute information such as measurement date and time, to the image processing server 5 via the communication network 7. A plurality of measuring terminals 1 can operate at the same time, and the hologram data collected by each measuring terminal 1 is collected in an image processing server 5 via the communication network 7. Incidentally, it is sufficient to send raw, in other words, unprocessed hologram data from each measuring terminal 1 to the server 5. However, if necessary, hologram data subjected to a processing process for correcting an error factor peculiar to each measuring terminal 1 may be sent to the server 5.

In the image processing server 5, the data transmitting/receiving unit 51 receives the hologram data sent from each measuring terminal 1, and stores the hologram data together with identification information for specifying the measuring terminal 1, identification information of the cell culture plate inputted at the time of photographing and attribute information such as photographing date and time in the measurement data storage unit 52.

After collecting data in this way, the arithmetic processing unit 53 reads the hologram data from the measurement data storage unit 52 appropriately, and executes a predetermined arithmetic processing to calculate phase information, intensity information, pseudo phase information, and the like of the entire observation target area. The pseudo phase information corresponds to the phase difference information including an intensity component obtained by the phase contrast microscope. Based on the phase information, the intensity information, and the pseudo phase information calculated from the hologram data, the image creation unit 54 creates a phase image, an intensity image, and a pseudo phase image of the entire observation target area. Known algorithms disclosed in Patent Literature 2 and the like may be used in calculating such phase information and creating the phase image.

Here, when creating the phase image (and other types of images) for the entire observation target area, the image creation unit 54 creates not only the highest resolution phase image which is obtained in principle from the obtained data but also a phase image of resolution (magnification) of plural stages with reduced resolution by binning processing or the like based on the highest resolution phase image. Then, the created plural images having different resolutions are stored in the image data storage unit 56. Thus, for each hologram data obtained for one cell culture plate 13, the image data forming the phase image, the intensity image, and the pseudo phase image of the entire observation target area whose resolutions are different from each other are stored in the image data storage unit 56.

Figure 4:
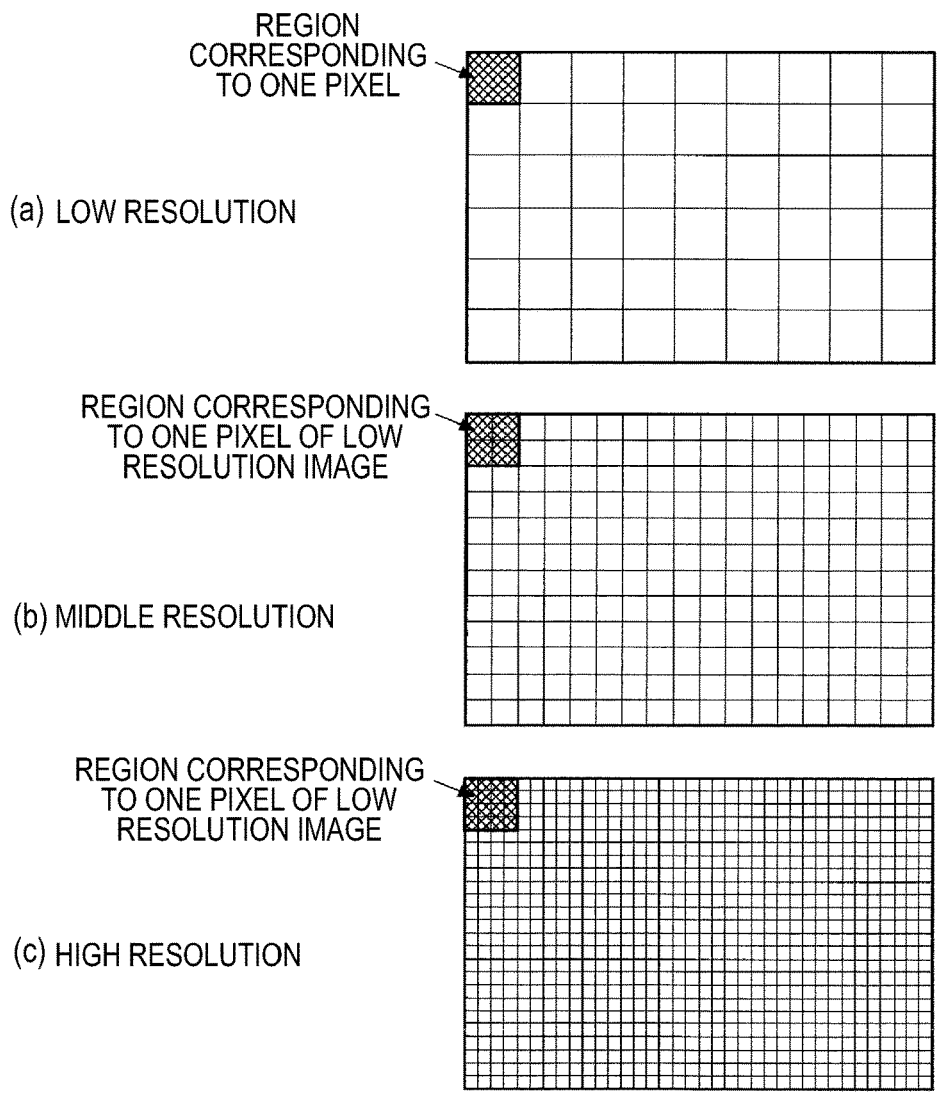
FIG. 4 is a schematic diagram illustrating images with different resolutions created on a server in the cell observation system of the present embodiment.

FIG. 4 is a schematic diagram illustrating an example of images created by the image creation unit 54 and having different resolutions. FIGS. 4(a), 4(b) and 4(c) are examples of images of low resolution, medium resolution, and high resolution with respect to the same observation target area, and one rectangular region segmented into a lattice shape in the figure corresponds to a pixel. In this example, one pixel of the low-resolution image (see FIG. 4(a)) corresponds to 4 pixels in the middle-resolution image (see FIG. 4(b)) and 16 pixels in the high-resolution image (see FIG. 4(c)). Since one phase value is associated with one pixel in the phase image, as a matter of course, a data amount for forming the phase image increases as the resolution increases. This also applies to the intensity image and the pseudo phase image.

Figure 5:
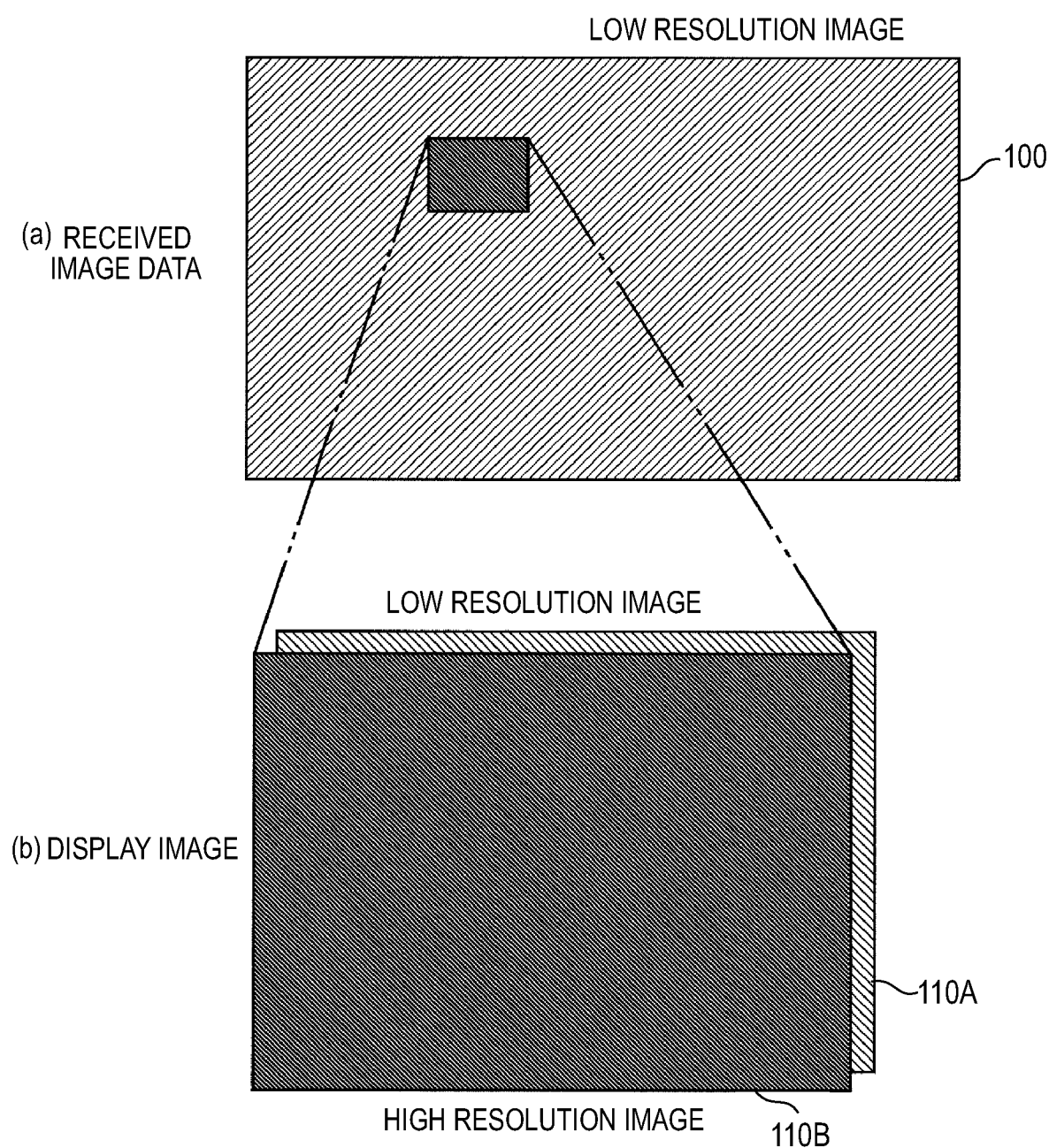
FIG. 5 is a conceptual diagram of image formation processing at a browsing terminal in the cell observation system of the present embodiment.
Figure 6:
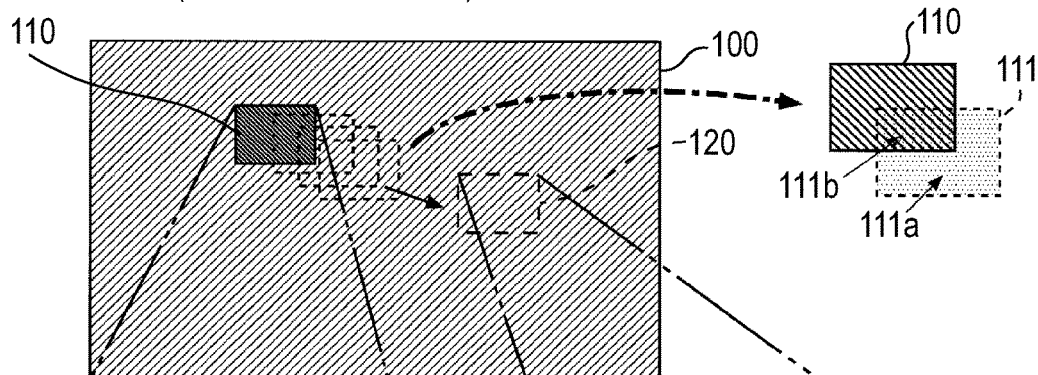
FIG. 6 is a conceptual diagram for describing an operation of image processing when an observation range is moved by a browsing terminal in the cell observation system of the present embodiment.
Figure 6:
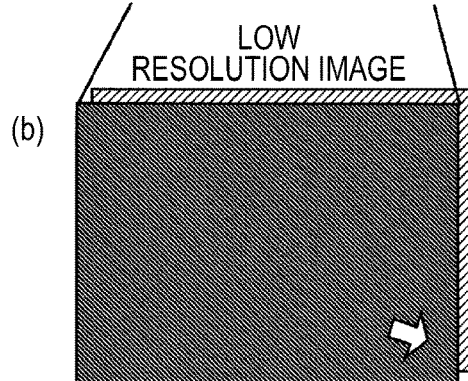
Figure 6:
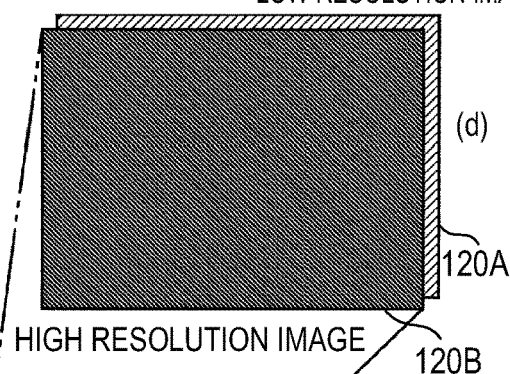
Figure 6:
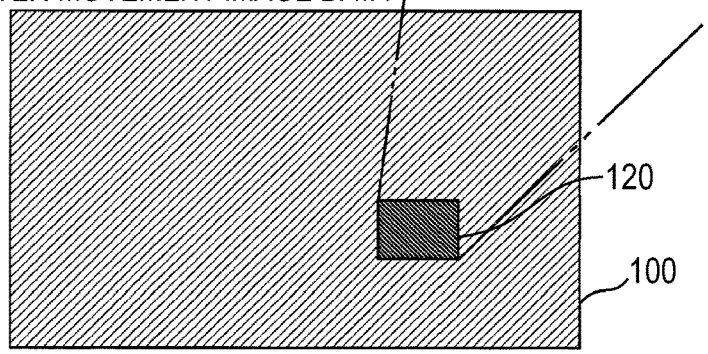

Next, operations when cell observation is performed in the browsing terminal 3 under the condition that the image data of a plurality of images with different resolutions are prepared in the image data storage unit 56 of the image processing server 5 as described above will be described with reference to FIGS. 5 and 6 in addition to FIGS. 1, 3 and 4. FIG. 5 is a conceptual diagram of an image forming process in the browsing terminal 3, and FIG. 6 is a conceptual diagram for describing the operation of the image processing when operations of moving an observation range in the browsing terminal 3 are made.

When an image specifying information such as an identification number of the cell culture plate and an image specifying information such as measurement date and time which the observer wishes to observe is input from the input unit 37 and a predetermined operation is performed by instructing a type (the phase image, the intensity image, etc.) of the image which the observer wishes to observe, the image display instruction receiving unit 33 receives the operation. For example, if the phase image is instructed as the type of image, the image transmission request unit 34 sends an image transmission request to the image processing server 5 via the communication network 7 so as to transfer the phase image instructed by the image specifying information. Upon receiving the image transmission request, the image transmission processing unit 55 in the server 5 reads the image data forming the phase image of the entire observation target area having the lowest resolution among the plurality of phase images having different resolutions corresponding to the designated image specifying information from the image data storage unit 56. Then, the data transmitting/receiving unit 51 transmits the image data to the browsing terminal 3 that issued the image transmission request. In the browsing terminal 3, the data transmitting/receiving unit 31 stores the image data transmitted from the image processing server 5 in the image data storage unit 32.

In the browsing terminal 3, the display image formation unit 35 uses the low-resolution phase image of the entire observation target area as a background, and overlays thereon a partial (that is, an area narrower than the entire observation target area) phase image having a higher resolution than that of the background to form a display image. Then, as soon as the image data forming the low-resolution phase image for the entire observation target area transmitted from the image processing server 5 is stored in the image data storage unit 2, the display image formation unit 35 forms a low-resolution background image on the basis of the image data. When the observer specifies to display the entire observation target area, there is no high-resolution image to be overlaid and the low-resolution phase image, as it is, is displayed as the display image on the screen of the display unit 25.

In a case where the observer designates to enlarge apart of the area in the observation target area, that is, to display at a high magnification, the image data forming the phase image with higher resolution of only the area to be displayed, in addition to the low-resolution image of the entire observation target area, is transmitted from the server 5. As illustrated in FIG. 5(a), the display image formation unit 35 overlays a high-resolution phase image corresponding to a narrow range (an observation range) 110 that the observer wishes to observe on a low-resolution phase image 100 with respect to the entire observation target area, and forms a display image corresponding to the observation range as illustrated in FIG. 5(b). The display image is one in which a high-resolution image 110B is overlaid on a low-resolution image 110A that corresponds to the observation range 110, a transmittance of the high-resolution image 110B is low and only the high-resolution image 110B actually appears in the display image on the screen of the display unit 38.

When the observer desires to move the observation range in the entire observation target area, that is, desires to observe an area different from the area of the display image being displayed on the screen of the display unit 38 at that point in the same resolution (without changing the magnification), the observer performs an operation of clicking the display image being displayed by a pointing device which is a part of the input unit 37 and then dragging it in a proper direction. As an example, it is assumed that the display image displayed on the screen of the display unit 38 is an image in which the high-resolution image 110B is overlaid on the low-resolution image 110A as illustrated in FIG. 6(b). It is assumed that, on this image, a drag operation has been performed in the direction indicated by the white arrow (roughly the lower right direction) in FIG. 6(b). Looking at the entire observation target area as illustrated in FIG. 6(a), this operation is to move the observation range from the observation range 110 of the low-resolution phase image 100 in the entire observation target area as indicated by a dotted line.

The image data forming the low-resolution phase image 100 of the entire observation target area is stored in the image data storage unit 32, whereas the image data forming the high-resolution image merely corresponds to the observation range 110 before the movement and is not stored in the image data storage unit 32. Therefore, as illustrated on the right of FIG. 6(a), while the observation range is being moved by the drag operation or the like, the display image formation unit 35 continues to display an image in which the high-resolution image is overlaid on the low-resolution image in a portion 111b including the observation range 110 before the movement to the observation range 111, whereas the display image formation unit 35 displays only the low-resolution image in a portion 111a not including the observation range 110 before the movement to the observation range 111.

When the drag operation by the observer is finished and a movement destination of the observation range is determined (an observation range 120 after the movement), the image transmission request unit 34 transmits the image transmission request together with position information (or information on the movement amount and the movement direction) indicating the observation range of the movement destination to the server 5. At this time, information on the number of pixels in the screen of the display unit 38 and the number of pixels determined by a size of an area of the screen on which the display image is displayed and the like may also be transmitted. Upon receiving the image transmission request, the image transmission processing unit 55 of the server 5 reads the image data of an appropriate resolution corresponding to the designated observation range 120 after the movement from the image data storage unit 56 and transmits the image data to the data transmitting/receiving unit 51. The browsing terminal 3 stores the received image data in the image data storage unit 32. The display image formation unit 35 overlays the high-resolution image 120B based on the image data on the low-resolution image 120A as a background and updates the display image with the image thus overlaid. Thus, on the screen of the display unit 38, the image corresponding to the observation range after the movement by the observer's operation is switched from the low-resolution image to the high-resolution image (see FIGS. 6(c), 6(d) and 6(e)).

What is transmitted from the server 5 to the browsing terminal 3 in the course of such series of operations of moving the observation range is only the image data for forming the high-resolution image corresponding to the observation range 120 after the movement, that is, the high-resolution image in a considerably narrow range compared to the entire observation target area, and no other image data is transmitted or received. Therefore, a transfer amount of the image data is small. Further, since the display image is obtained by forming the high-resolution image with respect to a much smaller range than the entire observation target area on the basis of the image data received by the display image formation unit 35 and overlaying the high-resolution image, it is possible to display a high-resolution phase image with high responsiveness, in other words, while suppressing a time delay from the operation.

Basically, the same operation is performed even when the observation range is enlarged or reduced instead of moving the observation range. However, the resolution does not change compared to that before the movement in the case of moving the observation range, but the resolution usually changes compared to that before the enlargement or reduction operation in the case of enlarging or reducing the observation range. Therefore, the image transmission processing unit 55 of the server 5 cuts out a partial image corresponding to the observation range from an image of the entire observation target area having an appropriate resolution according to a size of the observation range after the enlargement or reduction operation, and acquires and transmits the image data corresponding to the image thus cut out. Thus, the browsing terminal 3 also updates the image with high responsiveness during the enlargement or reduction operation.

In the above description, it is assumed that only one image such as the phase image is displayed on the screen of the display unit 38 in the browsing terminal 3 (see FIG. 7(a)), but a plurality of images can be displayed side by side simultaneously on the screen of the display unit 38 of the browsing terminal 3 in the cell observation system of this embodiment.

FIG. 7(b) illustrates an example in which two images 220A and 220B are displayed side by side in an image display window 200, and FIG. 7(c) illustrates an example in which up to four images 230A, 230B, 230C, and 230D are displayed side by side in the image display window 200.

The type of the image to be displayed can be designated from the input unit 37. For example, in the example of two-image split display illustrated in FIG. 7(b), the phase image and the intensity image, the phase image and the pseudo phase image or the like created on the basis of the same hologram data may be displayed side by side.

Even in this case, as in the above description, the observation range may be moved or enlarged and reduced, for example, by performing the click and drag operation by the pointing device on any image of the phase image or the intensity image displayed. At this time, it is convenient to synchronize operations on the two images. For example, the observer may perform a movement operation of the observation range on the phase image 220A displayed on the left side in FIG. 7(b). In response thereto, the phase image 220A may be updated to the high-resolution phase image of the movement destination and, in connection with the update of the phase image 220A, the intensity image 220B displayed on the right side in FIG. 7(b) may also be updated to the high-resolution intensity image of the same movement destination. This may be easily dealt with by the image transmission processing unit 55 in the image processing server 5 reading the image data corresponding to the observation range of the movement destination of both the phase image and the intensity image to transmit the image data to the browsing terminal 30.

Further, instead of displaying different kinds of images such as the phase image and the intensity image created on the basis of the same hologram data side by side, it is also possible to display phase images or intensity images side by side with respect to the same observation range acquired at different measurement dates and times for the same cell culture plate 13. This makes it possible to easily observe changes in cells every day after initiating the culture of pluripotent cells, for example.

As illustrated in FIGS. 7(b) and 7(c), even when two images or four images are displayed at the same time and the images are moved or enlarged/reduced in connection with each other, a transfer amount of image data between the browsing terminal 3 and the image processing server 5 is almost unchanged compared to the case of moving or enlarging/reducing one image as illustrated in FIG. 7(a). This is because if the size of the image display window 200 on the screen of the display unit 38 is the same, the number of pixels included in the display area for displaying one or more display images is basically the same and a total amount of the image data is almost the same, regardless of the number of images to be displayed in the image display window 200. Therefore, even if a plurality of types of images are displayed at the same time, and their movement or enlargement/reduction operations are interlocked, a responsiveness of the display hardly changes from that in a case where there is only one display image, and high responsiveness can be maintained.

In the cell observation system of the embodiment described above, the microscopic observation unit 10 is an inline type holographic microscope, but it can be replaced by another type of holographic microscope such as an off-axis type microscope or a phase shift type microscope. In such a case, it is not necessary to say that the algorithm for calculation of the phase information and the like executed by the arithmetic processing unit 53 is changed. Further, in the cell observation system according to the present invention, the phase contrast microscope can be used instead of the holographic microscope. In that case, the image observed in the browsing terminal 3 is a phase contrast microscopic image. Further, in the cell observation system according to the present invention, another kind of a microscope capable of observing cells may be used.

In addition, the above-described embodiments are merely examples of the present invention, and it goes without saying that even if changes, modifications, and additions are appropriately made within the spirit of the present invention, they are included in the scope of claims of the present invention.

The invention claimed is:

1. A cell observation system comprising a server capable of creating an image relating to an observation target on the basis of data obtained by a microscopic observation unit with respect to the observation target and a browsing terminal for browsing the image created by the server on a screen of a display unit, the server and the browsing terminal being connected via a communication network,
wherein the server includes:
a1) an image creation unit that creates images having different resolutions at a plurality of levels with respect to an entire observation target area to be observed by the microscopic observation unit on the basis of the data obtained by the microscopic observation unit, and stores the images in an image storage unit; and
a2) an image transmission processing unit that extracts image information of all or a part of the images having a predetermined resolution stored in the image storage unit and transmits the extracted image information to the browsing terminal, in response to an image transmission request from the browsing terminal, and
wherein the browsing terminal includes:
b1) an operation unit that allows a user to move a display range of the observation target displayed on the screen of the display unit by the user;
b2) an image transmission request unit that transmits the image transmission request to the server so as to transmit an image, formed by the extracted image information, according to a designated resolution and a designated display range after the movement by an operation using the operation unit;
b3) a storage unit that stores a low-resolution image having a relatively low resolution and corresponding to the entire observation target area or a range wider than the display range of the observation target displayed on the screen of the display unit at least at that point in the observation target area; and
b4) a display image formation unit that forms a display image on the basis of at least the low-resolution image until the extracted image information arrives from the server in response to the image transmission request after the movement by the operation using the operation unit, and forms another display image by overlaying on the low-resolution image a new high-resolution image having a relatively high resolution and corresponding to the display range of the observation target displayed on the screen of the display unit at that time based on the extracted image information when the extracted image information is obtained from the server in response to the image transmission request.

2. The cell observation system according to claim 1, wherein the microscopic observation unit is a holographic microscope, and the image creation unit creates at least one of a phase image, an intensity image or a pseudo phase image with respect to the entire observation target area on the basis of a hologram data obtained by the holographic microscope.

3. The cell observation system according to claim 2, wherein the server creates two or more kinds of cell observation images of the phase image, the intensity image, or the pseudo phase image,
wherein the browsing terminal simultaneously displays a plurality of types of cell observation images for the same area in the observation target area on the screen of the display unit, and moves the cell observation image and the displayed other cell observation images in conjunction with each other in response to an operation of the movement on any displayed cell observation image.

4. The cell observation system according to claim 3, wherein the image transmission processing unit transmits a size of a display area of each of the plurality of types of cell observation images displayed on the screen of the display unit of the browsing terminal and image information of a resolution corresponding to a screen resolution of the display unit to the browsing terminal.

5. The cell observation system according to claim 4, wherein the display image formation unit forms display images on the basis of image information acquired at different dates and times for the same area of the same observation target and displays the plurality of images simultaneously on the screen of the display unit.

6. The cell observation system according to claim 3, wherein the display image formation unit forms display images on the basis of image information acquired at different dates and times for the same area of the same observation target and displays the plurality of images simultaneously on the screen of the display unit.

7. The cell observation system according to claim 2, wherein the display image formation unit forms display images on the basis of image information acquired at different dates and times for the same area of the same observation target and displays the plurality of images simultaneously on the screen of the display unit.

8. The cell observation system according to claim 1, wherein the display image formation unit forms display images on the basis of image information acquired at different dates and times for the same area of the same observation target and displays the plurality of images simultaneously on the screen of the display unit.

* * * * *